United States Patent [19]

Inagaki et al.

[11] Patent Number: 4,767,692

[45] Date of Patent: Aug. 30, 1988

[54] SILVER HALIDE PHOTOGRAPHIC MATERIAL

[75] Inventors: Yoshio Inagaki; Morio Yagihara; Shigeo Hirano, all of Kanagawa, Japan

[73] Assignee: Fuji Photo Film Co., Ltd., Kanagawa, Japan

[21] Appl. No.: 484

[22] Filed: Jan. 5, 1987

[30] Foreign Application Priority Data

Jan. 9, 1986 [JP] Japan .................................. 61-2708

[51] Int. Cl.⁴ ........................ G03C 1/42; G03C 1/485
[52] U.S. Cl. .................................. 430/264; 430/217; 430/441; 430/442; 430/484; 430/598; 430/599; 430/566; 430/600; 430/603
[58] Field of Search ............... 430/598, 440, 441, 442, 430/484, 264, 566, 599, 600, 603

[56] References Cited

U.S. PATENT DOCUMENTS

| | | | |
|---|---|---|---|
| 4,245,037 | 1/1981 | Tsujino et al. | 430/598 |
| 4,255,511 | 3/1981 | Hirano et al. | 430/598 |
| 4,266,013 | 5/1981 | Adachi et al. | 430/598 |
| 4,323,643 | 4/1982 | Mifune et al. | 430/598 |
| 4,374,923 | 2/1983 | Hirano et al. | 430/598 |
| 4,385,108 | 5/1983 | Takagi et al. | 430/441 |
| 4,550,070 | 10/1985 | Miyasaka et al. | 430/598 |
| 4,681,836 | 7/1987 | Inoue et al. | 430/440 |

FOREIGN PATENT DOCUMENTS 0200231 11/1984 Japan .................................. 430/598

*Primary Examiner*—Richard L. Schilling
*Attorney, Agent, or Firm*—Sughrue, Mion, Zinn, Macpeak & Seas

[57] ABSTRACT

A novel silver halide photographic material is provided comprising a support and at least one silver halide photographic emulsion layer formed thereon and containing in said photographic emulsion layer or at least one hydrophilic colloid layer a compound represented by formula (I):

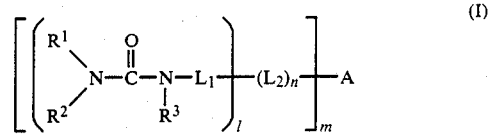

wherein $R^1$ and $R^2$ may be the same or different and each represents a hydrogen atom, an aliphatic residual group, an aromatic residual group, or a heterocyclic residual group; $R^3$ represents a hydrogen atom or an aliphatic residual group; $L_1$ represents a divalent aliphatic group, a divalent aromatic group, or a divalent heterocyclic group; $L_2$ represents —O—, —CONR—, —NRCO—, —SO₂NR—, —NRSO₂—, —OCO—, —COO—, —S—, —NR—, —CO—, —SO—, —SO₂—, —OCOO—, —NRCONR'—, —NRCOO—, —OCONR—, or —NRSO₂NR'— (in which R and R' each represents a hydrogen atom, an alkyl group or an aryl group); l and m each represents an integer of 1 or 2; n represents an integer of 0 or 1; and A represents a residual group which is obtained by removing hydrogen atoms from Ar or B in a compound represented by formula (II), provided that when m=1, one hydrogen atom is removed; when m=2, two hydrogen atoms are removed:

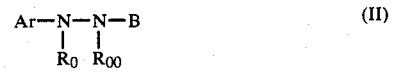

wherein Ar represents an aryl group; B represents a formyl group, an acyl group, an alkyl or arylsulfonyl group, an alkyl or arylsulfinyl group, a carbamoyl group, a sulfamoyl group, an alkoxy or aryloxycarbonyl group, a sulfinamoyl group, an alkoxysulfonyl group, a thioacyl group, a thiocarbamoyl group, or a heterocyclic group; and $R_0$ and $R_{00}$ each represents a hydrogen atom or one of $R_0$ and $R_{00}$ represents a hydrogen atom and the other represents a substituted or unsubstituted alkylsulfonyl group, a substituted or unsubstituted arylsulfonyl group or a substituted or unsubstituted acyl group, with the proviso that B, $R_{00}$ and the nitrogen atom to which B and $R_{00}$ are bonded may together form a partial structure of hydrazone (—N=C<).

4 Claims, No Drawings

SILVER HALIDE PHOTOGRAPHIC MATERIAL

FIELD OF THE INVENTION

The present invention relates to a silver halide photographic material that provides an extremely high contrast negative image, high sensitivity negative image, and excellent dot image or forms a direct positive photographic image to the silver halide photographic material. More particularly, the present invention relates to a photographic light-sensitive material containing a novel compound as a silver halide nucleating agent.

BACKGROUND OF THE INVENTION

The addition of a hydrazine compound to a silver halide photographic emulsion or developing solution is known in U.S. Pat. No. 3,730,727 (a developing solution obtained by combining ascorbic acid and hydrazine), U.S. Pat. No. 3,227,552 (the use of hydrazine as an auxiliary developing agent for obtaining a direct positive color image), U.S. Pat. No. 3,386,831 (containing β-monophenyl hydrazide of an aliphatic carboxylic acid as a stabilizer for a silver halide light-sensitive material), U.S. Pat. No. 2,419,975, and *The Theory of Photographic Process* (edited by Mees, 3rd Edition, 1966, page 281).

It is disclosed in this literature, particularly U.S. Pat. No. 2,419,975, that the addition of a hydrazine compound provides a high contrast negative image.

It is described in the above U.S. Pat. No. (2,419,975) specification that when a light-sensitive material comprising a silver chlorobromide emulsion containing a hydrazine is developed with a developing solution having a pH as high as 12.8, an extremely high contrast having a gamma value (γ) of more than 10 can be obtained. However, a strong alkali developing solution having a pH of near 13 is easily subject to oxidation by air and thus unstable for prolonged storage or use.

A superhigh contrast photographic property having a gamma value of more than 10 is extremely useful in the photographic reproduction of continuous tone images or line images produced by dot images useful for photomechanical process, whether the image is a negative or positive image. For such a purpose, a silver chlorobromide photographic emulsion having a silver chloride content of more than 50 mol %, and preferably 75 mol % has heretofore been used. Furthermore, the development has heretofore been conducted by using a hydroquinone developing solution having an extremely low effective concentration of sulfite ions (generally 0.1 mol/l or less). However, this process is disadvantageous in that the developing solution is extremely unstable and, thus, cannot withstand storage for a period of time exceeding 3 days because of its low concentration of sulfite ions.

Furthermore, this process cannot provide high sensitivity because it requires use of a silver chlorobromide emulsion having a relatively high content of silver chloride. Therefore, it had been keenly desired to obtain a superhigh contrast photographic property useful for reproduction of dot images or line images by using a high sensitivity emulsion and a stable developing solution.

The present inventors disclosed silver halide photographic emulsions which provide an extremely high contrast negative photographic property when developed with a stable developing solution in U.S. Pat. Nos. 4,224,401, 4,168,977, 4,243,739, 4,272,614, and 4,323,643. However, the present inventors found that acylhydrazine compounds used in these emulsions have some disadvantages.

That is, these conventional hydrazines are known to generate nitrogen gas during development. This nitrogen gas gathers in the film to form bubbles, to thereby reduce the quality of photographic images. Furthermore, when the gas flows into the developing solution, it has adverse influences on other photographic light-sensitive materials.

Furthermore, these conventional hydrazines are required in a large amount for increasing sensitization and contrast. If the light-sensitive material requires a high sensitivity in particular, and these conventional hydrazines are used in combination with other sensitizing techniques (e.g., enhancing chemical sensitization, using grains of larger size, or adding a compound for accelerating sensitization as described in U.S. Pat. Nos. 4,272,606 and 4,241,164), sensitization and fogging are accelerated with time during storage.

Therefore, a compound has been desired which eliminates generation of such bubbles and outflow of the bubbles into the developing solution causes no problems on stability with the passage of time, and provides an extremely high contrast photographic property with addition of an extremely small amount thereof.

It is described in U.S. Pat. Nos. 4,385,108 and 4,269,929 that the use of a hydrazine having a substituent which is easily adsorbed on the silver halide grains can provide an extremely high contrast negative gradation photographic property. Among these hydrazine compounds containing such an adsorptive group, those described in the above mentioned known examples are subject to desensitization with the passage of time during storage. Therefore, it is required to select compounds which cause no such problem.

On the other hand, there are various direct positive photographic processes among which two are the most useful. One is a process in which a previously fogged silver halide grain is exposed to light in the presence of a desensitizer, and then developed. The other is a process in which a silver halide emulsion containing a sensitive speck thereinside is exposed to light, and then developed in the presence of a nucleating agent. The present invention relates to the latter process. A silver halide emulsion which has a sensitive speck mainly inside silver halide grains so that a latent image is formed mainly inside the grains is called an internal latent image type silver halide emulsion and is distinguished from a silver halide grain which forms a latent image mainly on the surface thereof.

Examples of the process in which an internal latent image type silver halide photographic emulsion is surface-developed in the presence of a nucleating agent to obtain a direct positive image and photographic emulsions or light-sensitive materials to be used in such a process are found in U.S. Pat. Nos. 2,456,953, 2,497,875, 2,497,876, 2,588,982, 2,592,250, 2,675,318, 3,227,552 and 3,317,322, British Pat. Nos. 1,011,062, 1,151,363, 1,269,640 and 2,011,391, Japanese Patent Publication Nos. 29405/68 and 38164/74, and Japanese Patent Application (OPI) Nos. 16623/78, 137133/78, 79, 40629/79, 74536/79, 74729/79, 52055/80 and 90940/80 (the term "OPI" as used herein refers to a "published unexamined Japanese patent application").

In the process for obtaining a direct positive image, the nucleating agent may be added to the developing solution. However, a better reversal effect can be obtained by adding the nucleating agent to a photographic emulsion layer in the light-sensitive material or other proper layers so that it is adsorbed on the surface of the silver halide grain.

As suitable nucleating agents which may be used in the above process for obtaining a direct positive image there are known hydrazines as described in U.S. Pat. Nos. 2,563,785 and 2,588,982, hydrazide and hydrazine compounds as described in U.S. Pat. No. 3,227,552, heterocyclic quaternary salt compounds as described in U.S. Pat. Nos. 3,615,615, 3,719,494, 3,734,738, 4,094,683 and 4,115,122, British Pat. No. 1,283,835 and Japanese Patent Application (OPI) Nos. 3426/77 and 69613/77, thiourea combined type acylphenylhydrazine compounds as described in U.S. Pat. Nos. 4,030,925, 4,031,127, 4,139,387, 4,245,037, 4,255,511 and 4,276,364, and British Pat. No. 2,012,443, compounds having a heterocyclic thioamide in an adsorptive group as described in U.S. Pat. No. 4,080,207, phenylacylhydrazine compounds containing a heterocyclic group having a mercapto group as an adsorption group as described in British Pat. No. 2,011,397B, sensitizing dyes containing in the molecular structure a substituent having a nucleating action as described in U.S. Pat. No. 3,718,470, and hydrazine compounds as described in Japanese Patent Application (OPI) Nos. 200230/84, 212828/84 and 212829/84, and *Research Disclosure*, No. 23510 (November, 1953).

However, it has been found that these compounds do not have sufficient activity for nucleating agents. Furthermore, it has been found that those having a high activity are poor in shelf life.

SUMMARY OF THE INVENTION

It is, therefore, an object of the present invention to provide a silver halide photographic material which can provide an extremely high contrast negative gradation photographic property having a gamma value of more than 10 when developed with a stable developing solution.

It is another object of the present invention to provide a negative type silver halide photographic material containing an acylhydrazine which can provide a desired extremely high contrast negative gradation photographic property when used in a small amount without having adverse influences on the photographic property.

It is a further object of the present invention to provide a direct positive type silver halide photographic material containing a highly active nucleating agent.

It is a still further object of the present invention to provide a silver halide photographic material excellent on stability with the passage of time containing an acylhydrazine which can be easily synthesized and is excellent in shelf life.

These and other objects of the present invention will become more apparent from the following detailed description and examples.

These objects of the present invention are accomplished by providing a silver halide photographic material comprising a support and at least one silver halide photographic emulsion layer formed thereon and containing in the photographic emulsion layer or at least one hydrophilic colloid layer a compound represented by formula (I):

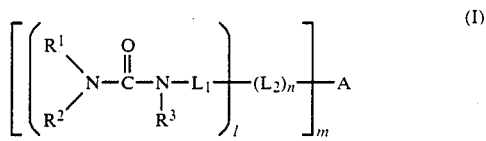

wherein $R^1$ and $R^2$ may be the same or different and each represents a hydrogen atom, an aliphatic residual group, an aromatic residual group, or a heterocyclic residual group; $R^3$ represents a hydrogen atom or an aliphatic residual group; $L_1$ represents a divalent aliphatic group, a divalent aromatic group, or a divalent heterocyclic group; $L_2$ represents —O—, —CONR—, —NRCO—, —SO$_2$NR—, —NRSO$_2$—, —OCO—, —COO—, —S—, —NR—, —CO—, —SO—, —SO$_2$—, —OCOO—, —NRCONR'—, —NRCOO—, —OCONR—, or —NRSO$_2$NR'—(in which R and R' each represents a hydrogen atom, an alkyl group or an aryl group); l and m each represents an integer of 1 or 2; n represents an integer of 0 or 1; and A represents a residual group which is obtained by removing hydrogen atoms from Ar or B in a compound represented by formula(II), provided that when m=1, one hydrogen atom is removed; when m=2, hydrogen atoms are removed:

wherein Ar represents an aryl group; B represents a formyl group, an acyl group, an alkyl or arylsulfonyl group, an alkyl or arylsulfinyl group, a carbamoyl group, a sulfamoyl group, an alkoxy or aryloxycarbonyl group, a sulfinamoyl group, an alkoxysulfonyl group, a thioacyl group, a thiocarbamoyl group, or a heterocyclic group; and $R_0$ and $R_{00}$ each represents a hydrogen atom or one of $R_0$ and $R_{00}$ represents a hydrogen atom and the other represents a substituted or unsubstituted alkylsulfonyl group, a substituted or unsubstituted arylsulfonyl group, or a substituted or unsubstituted acyl group, with the proviso that B, $R_{00}$ and the nitrogen atom to which B and $R_{00}$ are bonded can together form a partial structure of hydrazone (—N=C<).

Preferred among the compounds represented by formula (I) are compounds represented by formulae (III) or (IV):

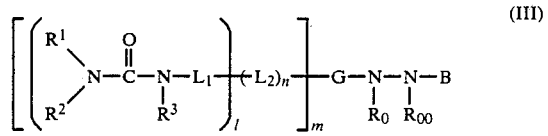

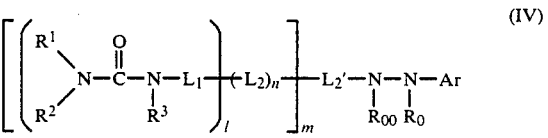

wherein $R^1$, $R^2$, $R^3$, $L_1$, $L_2$, l, m, n, Ar, $R_0$, $R_{00}$ and B are as defined in formula (I); G represents a group formed by removing one hydrogen atom from Ar in formula (II) (i.e., an arylene group); and $L_2'$ represents —CO—, —SO—, or —SO$_2$—.

DETAILED DESCRIPTION OF THE INVENTION

In formulae (I), (III) and (IV), $L_1$ represents a divalent organic group (preferably having from 1 to 30 carbon atoms), including a divalent aliphatic group, a divalent aromatic group, and a divalent heterocyclic group. Specifically, $L_1$ is formed by a divalent group such as an alkylene group, an alkenylene group, —O—, —S—, —CO—, —SO—, —SO$_2$—, and an imino group, singly or in combination. Specific examples of $L_1$ are shown hereinafter.

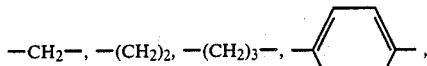

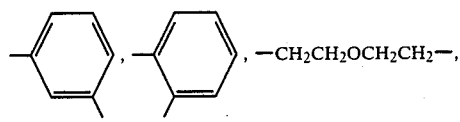

—CH$_2$CH$_2$SCH$_2$CH$_2$—, —CH$_2$CH$_2$CONHCH$_2$CH$_2$—,

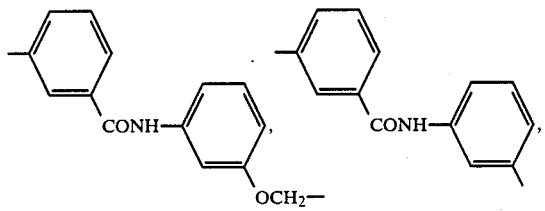

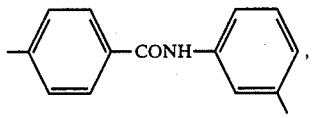

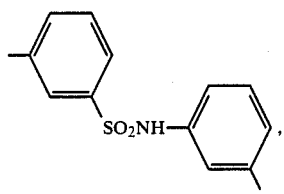

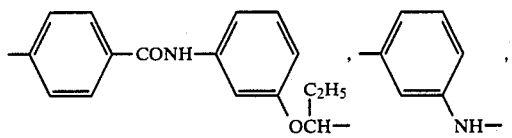

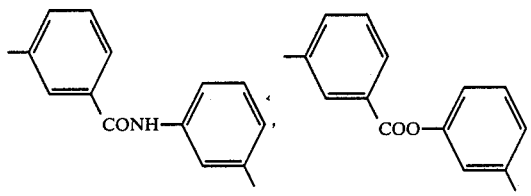

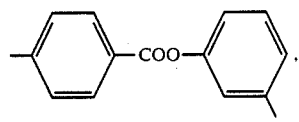

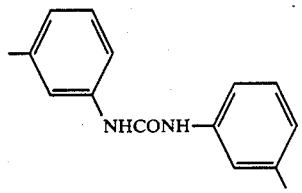

In formulae (I), (III) and (IV), $L_2$ is preferably —CONR—, —SO$_2$NR— or —NRCONR'—.

In $L_2$, R and R' each represents a hydrogen atom, an alkyl group (preferably a lower alkyl group (particularly preferably having from 1 to 8 carbon atoms) such as a methyl group and an ethyl group), or an aryl group (preferably a phenyl group) optionally containing a substituent as described below.

In formula (IV), $L_2'$ is most preferably —CO—.

In formulae (II) and (IV), the aryl group represented by Ar is preferably a phenyl group or a naphthyl group.

In formula (III), G is an arylene group which is obtained by removing hydrogen atoms (when m=1, one hydrogen atom is removed; when m=2, two hydrogen atoms are removed) from the aryl group represented by Ar.

The aryl group represented by Ar and the arylene group represented by G may optionally contain a substituent. Examples of substituents described above include an alkyl group such as a methyl group and an ethyl group; a halogen atom such as F, C, and Br; an alkoxy group such as a methoxy group and a methoxyethoxy group; a carbonamide group such as an acetamide group; and a sulfonamide group such as a methanesulfonamide group.

In formulae (II), (III) and (IV), $R_0$ and $R_{00}$ each specifically represents a hydrogen atom, an alkylsulfonyl group or an arylsulfonyl group having 20 or less carbon atoms (preferably a phenylsulfonyl group or a phenylsulfonyl group which is substituted in such a manner that the sum of Hammett's substituent constant is —0.5 or more), an acyl group having 20 or less carbon atoms (preferably a benzoyl group or a benzoyl group which is substituted in such a manner that the sum of Hammett's substituent constant is —0.5 or more), or a straight chained, branched or cyclic substituted or unsubstituted acyl group. Examples of such a substituent for the substituted acyl group include a halogen atom, an ether group, a sulfonamide group, a carbonamide group, a hydroxyl group, a carboxyl group and a sulfonic acid group.

$R_0$ and $R_{00}$ each is most preferably a hydrogen atom.

In formulae (II) and (III), B specifically represents a formyl group; an acyl group such as an acetyl group, a 2-hydroxyphenylacetyl group, a propionyl group, a trifluoroacetyl group, a chloroacetyl group, a benzoyl group, a 4-chlorobenzoyl group, a pyruvoyl group, a methoxalyl group, and a methyloxamoyl group; an alkylsulfonyl group such as a methanesulfonyl group and a 2-chloroethanesulfonyl group; an arylsulfonyl group such as a benzenesulfonyl group; an alkylsulfinyl group such as a methanesulfinyl group; an arylsulfinyl group such as a benzenesulfinyl group; a carbamoyl group such as a methylcarbamoyl group and a phenylcarbamoyl group; a sulfamoyl group such as a dimethylsulfamoyl group; an alkoxycarbonyl group such as a methoxycarbonyl group and a methoxyethoxycarbonyl group; an aryloxycarbonyl group such as a phenoxycarbonyl group; a sulfinamoyl group such as a methylsulfinamoyl group; an alkoxysulfonyl group such as a methoxysulfonyl group and an ethoxysulfonyl group; a thioacyl group such as a methylthiocarbonyl group; a thiocarbamoyl group such as a methylthiocarbamoyl group; or a heterocyclic group such as a pyridine ring.

B is most preferably a formyl group or an acyl group.

In formulae (II) and (III), $R_{00}$ may form a partial structure of hydrazone

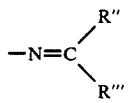

together with B and a nitrogen atom to which $R_{00}$ and B are bonded. That is, formula (III) is represented by formula (V):

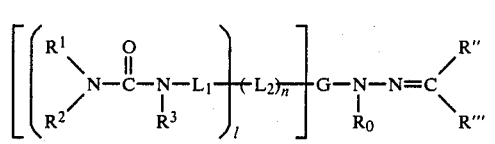

In formulae (II) and (IV), $R_{00}$ may form a partial structure of hydrazone

together with $L_2'$ and a nitrogen atom to which $R_{00}$ and $L_2'$ are bonded. That is, formula (IV) is represented by formula (VI):

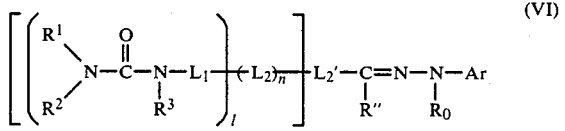

In the above description, R" represents an alkyl group, an aryl group or a heterocyclic group, and preferably a substituted or unsubstituted alkyl group having from 1 to 20 carbon atoms or a substituted or unsubstituted phenyl group having from 6 to 20 carbon atoms; R'" represents a hydrogen atom, an alkyl group, an aryl group or a heterocyclic group, and preferably a hydrogen atom, a substituted or unsubstituted alkyl group having from 1 to 20 carbon atoms, or a substituted or unsubstituted phenyl group having from 6 to 20 carbon atoms.

Examples of hydrazone formed by $R_{00}$ and B or $L_2'$ include acetonehydrazone, benzaldehydehydrazone, and o-hydroxybenzaldehydehydrazone.

$R_{00}$ is most preferably a hydrogen atom.

In formulae (I), (III) and (IV), specific examples of the aliphatic residual group represented by $R^1$ or $R^2$ include a straight chained or branched alkyl group, a cycloalkyl group, and those having a substituent thereon, an alkenyl group, and an alkynyl group. Examples of such straight chained and branched alkyl groups include alkyl groups having from 1 to 36 carbon atoms, and preferably from 1 to 20 carbon atoms. Specific examples of such alkyl groups include a methyl group, an ethyl group, an isobutyl group, a t-octyl group, etc.

Examples of the above mentioned cycloalkyl group include cycloalkyl groups having from 3 to 20 carbon atoms. Specific examples of such cycloalkyl groups include a cyclopentyl group, a cyclohexyl group, an adamantyl group, etc. Examples of the substituent for these alkyl groups and cycloalkyl groups include an alkoxy group such as a methoxy group, an ethoxy group, a butoxy group, etc.; a phenoxy group; a halogen atom such as chlorine, bromine, fluorine, iodine, etc.; an alkoxycarbonyl group; an aryl group such as a phenyl group, etc., a halogen-substituted phenyl group, an alkoxyphenyl group, an alkylphenyl group, etc.; a hydroxyl group; a cyano group; a sulfonyl group, and the like. Examples of the substituted aliphatic group include a 3-methoxypropyl group, a 4-chlorocyclohexyl group, a benzyl group, a p-methylbenzyl group, a p-chlorobenzyl group, a 3-phenoxypropyl group, a 3-(2,4-di-t-pentylphenoxy)propyl group, and the like. Examples of the alkenyl group include an allyl group. Examples of the alkynyl group include a propargyl group.

On the other hand, the aromatic residual group represented by $R^1$ and $R^2$ includes a phenyl group, a naphthyl group, and those containing a substituent such as an alkyl group, an alkoxy group, an acylhydrazino group, a dialkylamino group, an alkoxycarbonyl group, a cyano group, a carboxyl group, a nitro group, an alkylthio group, a hydroxyl group, a sulfonyl group, a carbamoyl group, a halogen atom, etc. Specific examples of phenyl groups or naphthyl groups containing such a substituent include a p-methoxyphenyl group, an o-methoxyphenyl group, a tolyl group, a p-formylhydrazino group, a p-chlorophenyl group, an m-fluorophenyl group, etc.

Examples of the heterocyclic residual group represented by $R^1$ or $R^2$ include 5-membered or 6-membered monocyclic or condensed rings containing at least one of an oxygen atom, a nitrogen atom, a sulfur atom, and a selenium atom and those optionally containing a substituent. Specific examples of such a heterocyclic residual group include a pyrroline ring, a pyridine ring, a quinoline ring, an indole ring, an oxazole ring, a benzoxazole ring, a naphthoxazole ring, an imidazole ring, a benzimidazole ring, a thiazoline ring, a thiazole ring, a benzothiazole ring, a naphthothiazole ring, a selenazole ring, a benzoselenazole ring, a naphthoselenazole ring, and the like.

These heterocyclic groups may be substituted by an alkyl group having from 1 to 20 carbon atoms such as a methyl group, an ethyl group, etc.; an alkoxy group having from 1 to 20 carbon atoms such as a methoxy group, an ethoxy group, etc.; an aryl group such as a phenyl group, etc.; a halogen atom such as a chlorine atom, a bromine atom, etc.; an alkoxycarbonyl group; a cyano group; an amide group; or the like.

Either $R^1$ or $R^2$ is preferably a hydrogen atom.

Examples of the aliphatic residual group represented by $R^3$ include a straight chained or branched alkyl group, a cycloalkyl group and those containing a substituent thereon, an alkenyl group, and an alkynyl group. Examples of the straight chained or branched alkyl group include alkyl groups having from 1 to 36 carbon atoms, and preferably from 1 to 20 carbon atoms. Specific examples of such alkyl groups include a methyl group, an ethyl group, an isopropyl group, and the like. Examples of the cycloalkyl group include cycloalkyl groups having from 3 to 20 carbon atoms. Specific examples of such cycloalkyl groups include a cyclopentyl group, a cyclohexyl group, and the like. Examples of the substituent for the substituted alkyl or cycloalkyl group include an alkoxy group such as a methoxy group, an ethoxy group, etc.; an alkoxycarbonyl group; an aryl group such as a phenyl group, etc., a halogen-substituted phenyl group, an alkoxyphenyl group, an alkylphenyl group, etc.; an amide group; a phenoxy group; an alkyl-substituted phenoxy group; an acyloxy group; and the like. Specific examples of the substituted alkyl group or cycloalkyl group include a 3-methoxypropyl group, a benzyl group, a p-chlorobenzyl group, a p-methoxybenzyl group, a p-methylbenzyl group, a 3-phenoxypropyl group, a 3-(2,4-di-t-pentylphenoxy)propyl group, and the like. Examples of the alkenyl group include alkenyl groups having from 3 to 20 carbon atoms. Examples of such an alkenyl group include an allyl group and a 2-butenyl group. $R^3$ is most preferably a hydrogen atom.

Specific examples of compounds represented by formulae (I), (III) and (IV) useful in the present invention will be shown hereinafter, but should not be construed as limiting the present invention.

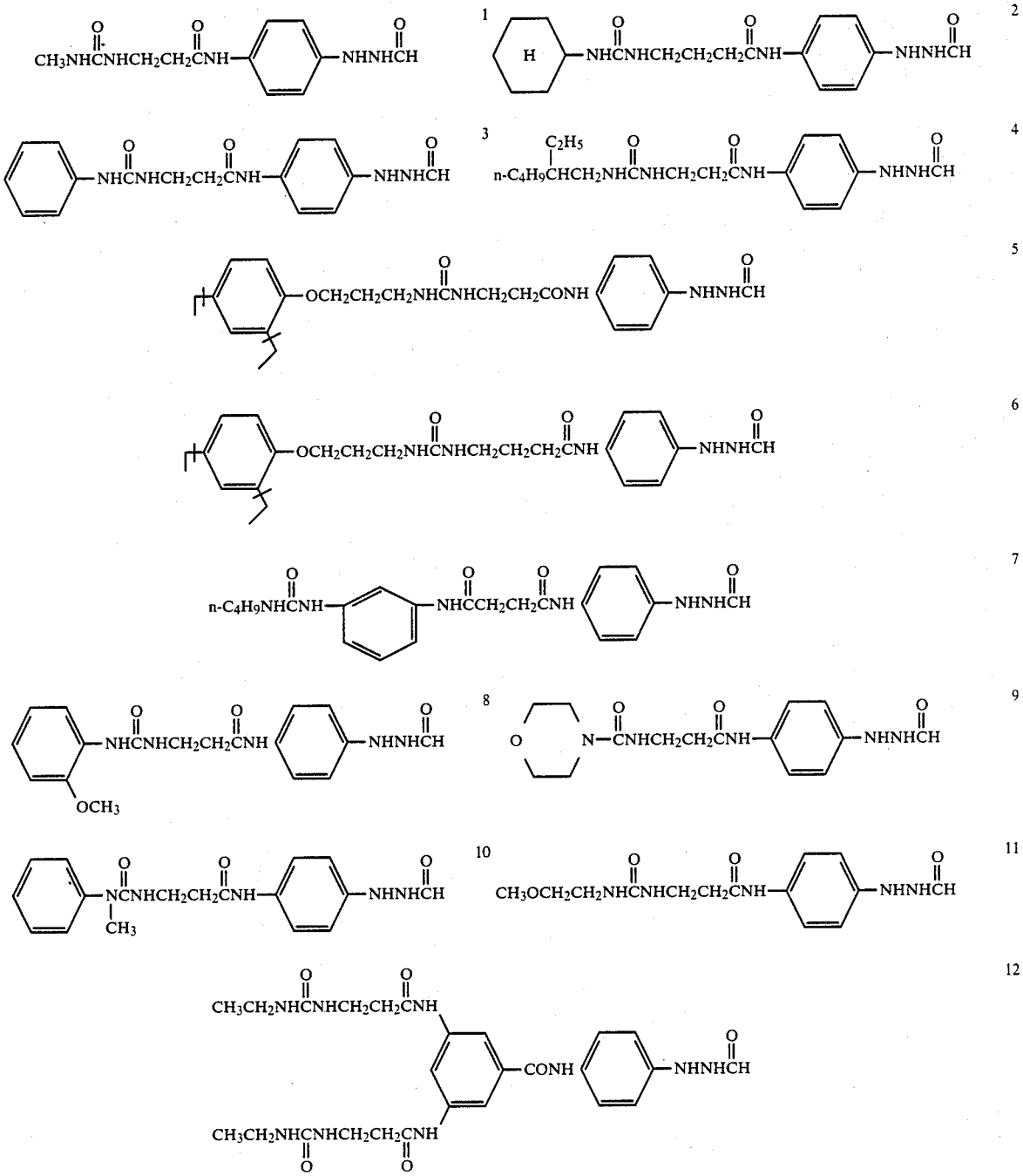

-continued
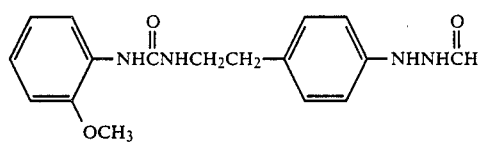 13
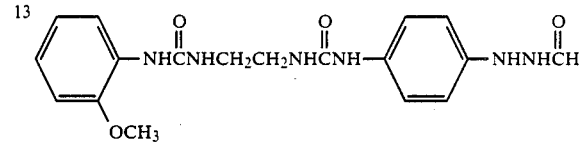 14
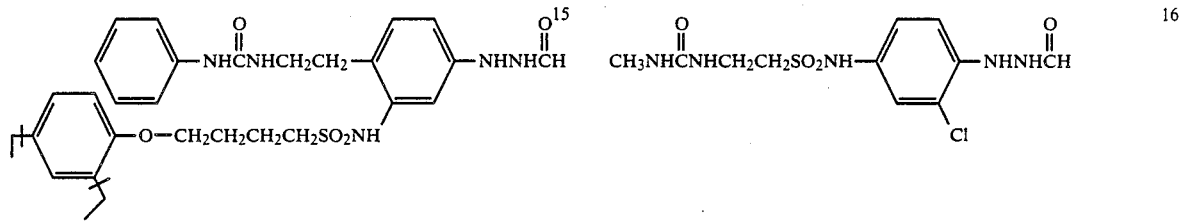 15
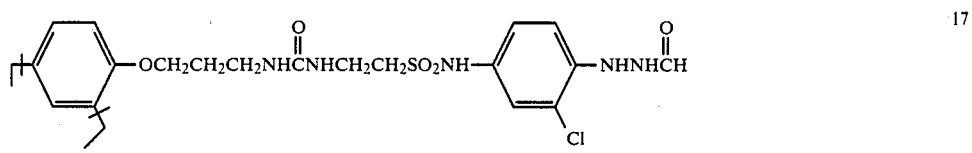 16
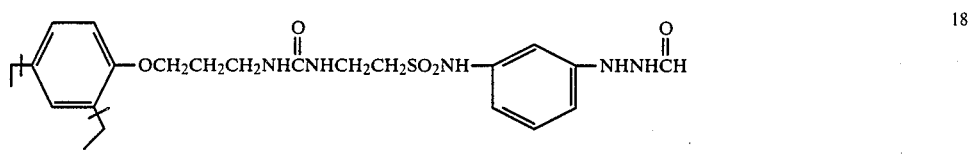 17
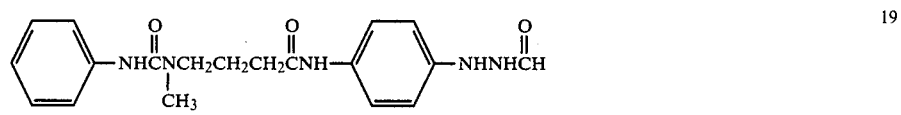 18
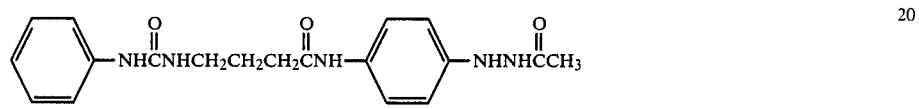 19
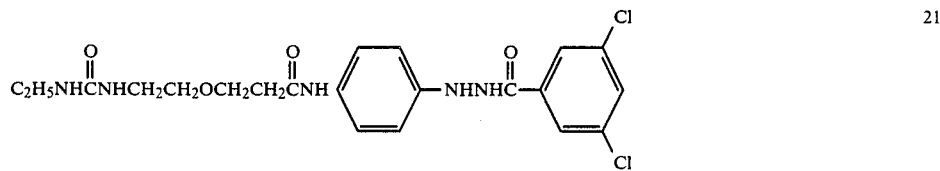 20
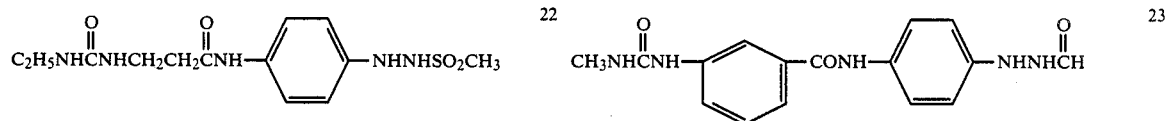 21
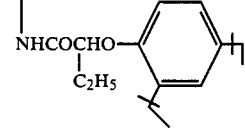 22
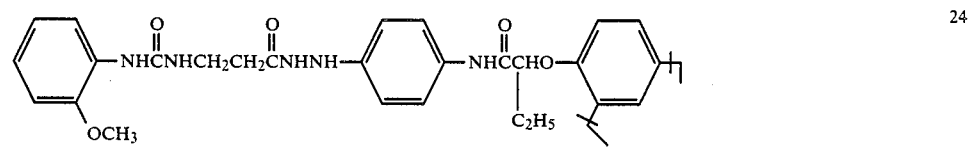 23
24

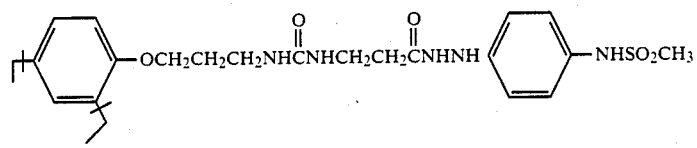

25

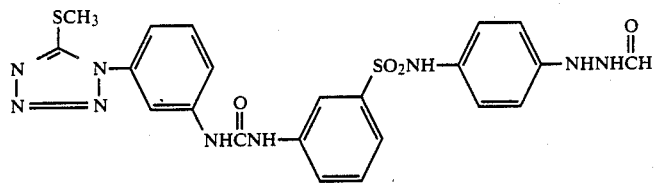

26

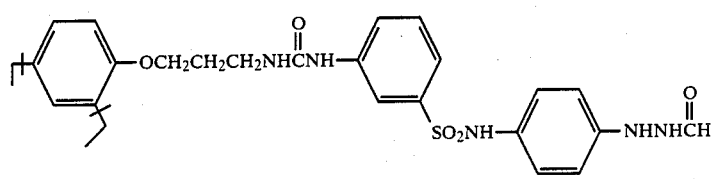

27

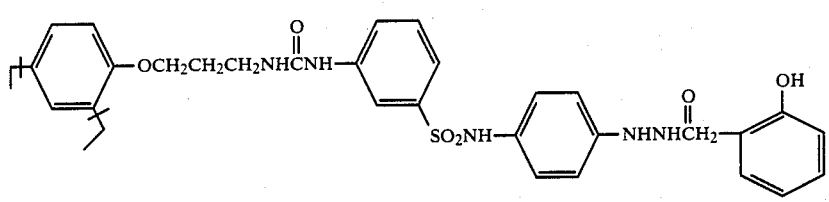

28

The present compounds can be synthesized by various methods. For examaple, if in formula (III), l=m=1, $L_2$ is —CONH— and G is a phenylene group, the present compounds can be synthesized by the following steps:

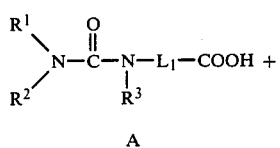

A

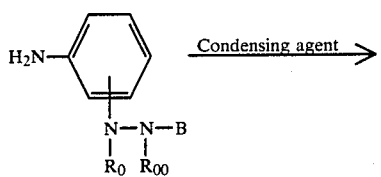

B

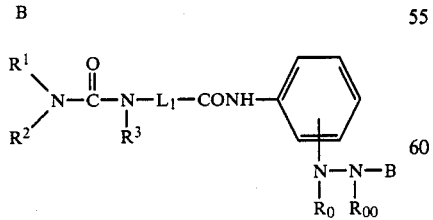

If $R^2$ is a hydrogen atom, the present compound can also be synthesized by the following steps:

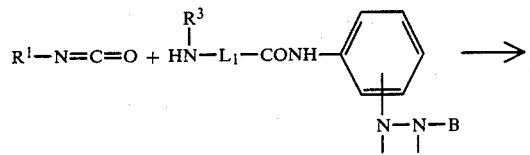

C        D

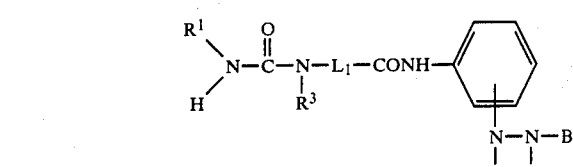

If in formula (IV), $L_2'$ is —CO—, the present compounds can also be synthesized by the following steps:

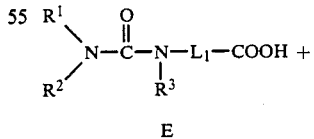

E

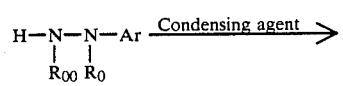

F

-continued

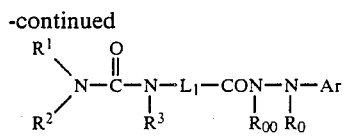

The above condensation reaction can be effected by using a condensing agent such as dicyclohexylcarbodiimide or carbonyldiimidazole in a solvent such as acetonitrile, tetrahydrofuran, dioxane, methylene chloride, chloroform, dimethylformamide, and dimethylacetamide. A catalyst such as 4-(N,N-dimethylamino)-pyridine, pyrrolidinopyridine, and N-hydroxybenzotriazole or a base such as triethylamine, N-ethylpiperidine, N-ethylmorpholine, and pyridine can be used in combination with the condensing agent for purposes of improving yield, shortening reaction time, or the like. Besides these reactions, the following reaction can be used. That is, A or E is rendered a mixed acid anhydride by a chloroformate such as ethyl chloroformate and isobutyl chloroformate in the presence of a base such as pyridine and triethylamine in a solvent such as dimethylformamide and dimethylacetamide, and the mixed acid anhydride thus formed undergoes a condensation reaction with an aniline compound B or a hydrazine compound F to obtain the desired product. Examples of methods of synthesis of such an aniline compound are described in Japanese Patent Application (OPI) No. 74729/79. The formation of the ureido bond by using the compound C (e.g., isocyanate) can be accomplished by reaction in an inert solvent such as toluene, carbon tetrachloride, tetrahydrofuran, and acetonitrile in accordance with the ordinary method.

The synthesis of the present compounds will be further described in the following specific examples:

SYNTHESIS EXAMPLE 1

Synthesis of Exemplary Compound 5:

10 ml of N,N-dimethylacetamide and 0.9 ml of triethylamine were added to 2.5 g of 3-[3-(2,4-di-t-pentylphenoxy)propylcarbamoylamino]propionic acid. The admixture was cooled to a temperature of −15° C. 0.61 ml of ethyl chloroformate was added dropwise to the solution in such a manner that the liquid temperature did not exceed −5° C. The admixture was then stirred at a temperature of −10° C. for 15 minutes. 0.97 g of 2-(4-aminophenol)-1-formylhydrazine was dissolved in 7 ml of N,N-dimethylacetamide. The resolution was added to the above solution. The admixture was stirred at a temperature of −30° C. for 30 minutes and then at room temperature for 30 minutes. A 2 wt % aqueous solution of sodium hydrogencarbonate which had been ice-cooled was poured into the solution. The resulting crystal was filtered off and washed with water. The crystal was recrystallized from 25 ml of acetonitrile. Yield: 1.9 g, melting point: 181.5° C.

SYNTHESIS EXAMPLE 2

Synthesis of Exemplary Compound 26:

2.3 g of 1-(3-isocyanatophenyl)-5-methylthiotetrazole was obtained from 2.4 g of 1-(3-aminophenyl)-5-methylthiotetrazole in almost the same manner as used in Synthesis Example 1. The compound thus obtained was allowed to react with 3.1 g of 2-(3-aminobenzenesulfonamidophenyl)-1-formylhydrazine in 15 ml of dimethylformamide at room temperature for 1 hour. Water was added to the reaction system. The resulting crystal was filtered off. The crystal thus obtained was then recrystallized from a mixed solvent of dimethylformamide and methanol (the ratio: 10/1). Yield: 4.4 g (in 80% yield), melting point: 208°–210° C. (decomposition)

SYNTHESIS EXAMPLE 3

Synthesis of Exemplary Compound 27:

A solution of 6.5 g of 3-(2,4-di-tert-amylphenoxy)-propylamine and 4.5 g of triethylamine which were dissolved in 10 ml of ethyl acetate was added dropwise to a solution of 2.3 g of trichloromethyl chloroformate which was dissolved in 50 ml of ethyl acetate while stirring under cooling in an ice bath. The admixture was further allowed to undergo reaction for 2 hours, and the resulting solid product was then filtered off. The filtrate was concentrated. 6.7 g of 2-(3-aminobenzenesulfonamidophenyl)-1-formylhydrazine which had been obtained by reacting 2-(4-aminophenyl)-1-formylhydrazine with m-nitrobenzenesulfonyl chloride and then by neutrality-reducing the product with iron powder was added to the filtrate thus concentrated. The admixture was then stirred in 30 ml of dimethylformamide under heating at a temperature of 30° C. After being allowed to undergo reaction for 2 hours, water was added to the solution to separate a rubber-like solid therefrom. The product was purified by means of a silica gel column chromatography (developing solvent: a mixed solvent of chloroform and methanol; mixing ratio: the ratio is changed from 20/1 to 10/1) to obtain 4.5 g of the desired compound. Yield: 33%, softening point: 120° C.

In the present invention, when the compound of formula (I) is incorporated in the photographic light-sensitive material, it may be dissolved in an organic solvent compatible with water such as alcohols (e.g., methanol and ethanol), esters (e.g., ethyl acetate), and ketones (e.g., acetone) or dissolved in water if it is water-soluble, and then added to a hydrophilic colloid solution.

The addition of the present compound to the photographic emulsion may be carried out at any stage between chemical ripening and coating. Preferably, it is carried out after chemical ripening is finished.

In the present invention, a silver halide light-sensitive material to be used in the formation of a high contrast image has at least one emulsion layer comprising a negative type silver halide emulsion.

The silver halide emulsion to be used in the present invention may have any suitable composition such as silver chloride, silver chlorobromide, silver iodobromide, and silver iodochlorobromide. However, the present silver halide emulsion is preferably a silver halide comprising 70 mol %, more preferably 90 mol % of silver bromide. The content of silver iodide is 10 mol % or less, preferably 0.1 to 5 mol %.

The silver halide grains in the photographic emulsion to be used in the present invention may have a relatively wide distribution of grain size but preferably have a narrow distribution of grain size. In particular, the size of 95% by weight or number of silver halide grains are preferably within ±40% of the average grain size. (In general, such an emulsion is called a monodispersed emulsion.)

The silver halide grains to be used in the present invention are preferably in the form of finely divided grains (e.g., grains having a grain size of 0.7 μm or less), more preferably in a size of 0.5 μm or less.

The silver halide grains in the photographic emulsion may be in the form of a regular crystal such as cubic, octahedral, etc., or an irregular crystal such as spherical, tabular, etc. Alternatively, they may be in the form of a composite of these crystal forms. Furthermore, they may be in the form of a mixture of various crystal forms.

The silver halide grains of the present invention comprise a phase which is uniform or different from the surface to the inside thereof.

Two or more silver halide emulsions which have been separately formed may be used in admixture.

A cadmium salt, a zinc salt, a lead salt, a thallium salt, an iridium salt or a complex salt thereof, a rhodium salt or a complex salt thereof, or an iron salt or a complex salt thereof may coexist with the silver halide emulsion to be used in the present invention in the step of formation of the silver halide grains or physical ripening.

In particular, a rhodium salt or a complex salt thereof is preferably used because it further improves adaptability of the photographic light-sensitive material to rapid processing. In general, as such a rhodium salt there may be used rhodium chloride, rhodium trichloride, or rhodium ammonium chloride. Alternatively, a complex salt thereof may be used. The addition of the rhodium salt may be effected before the first ripening in the step of preparation of the emulsion is finished. In particular, it is preferably effected during the formation of the emulsion grains. The amount of the rhodium salt to be added is preferably in the range of $1 \times 10^{-8}$ to $8 \times 10^{-5}$ mol, more preferably $1 \times 10^{-7}$ to $5 \times 10^{-6}$ mol per mol of silver of the emulsion.

In general, the addition of a rhodium salt to a silver halide emulsion causes a reduction in sensitivity as well as high contrast. However, with the presence of the compound of formula (I), the present emulsion can have its sensitivity recovered while providing a remarkably high contrast.

In order to obtain a higher sensitivity and a higher $\gamma$ value, the present emulsion is preferably prepared in the presence of an iridium salt or a complex salt thereof in an amount of $1 \times 10^{-8}$ to $1 \times 10^{-5}$ mol per mol of silver of the emulsion. Furthermore, silver haloiodide in which the content of silver iodide on the surface of grains is larger than that of the average value is preferably used.

The above mentioned amount of an iridium salt is preferably added before physical ripening, particularly during the formation of grains in the step of preparation of the silver halide emulsion.

As such an iridium salt, there may be used a water-soluble iridium salt or an iridium complex salt. Examples of such an iridium salt include iridium trichloride, iridium tetrachloride, potassium hexachloroiridiumate (III), potassium hexachloroiridiumate (IV), and ammonium hexachloroiridiumate (III).

The amount of the compound represented by formula (I) to be used for a high contrast light-sensitive material is preferably from $1 \times 10^{-6}$ to $5 \times 10^{-2}$ mol, more preferably from $1 \times 10^{-5}$ to $2 \times 10^{-2}$ mol per mol of silver in the silver halide emulsion.

As a binder or protective colloid for the present photographic emulsion, gelatin is advantageously used. However, other hydrophilic colloids can also be used. For example, various synthetic hydrophilic high molecular substances such as gelatin derivatives; graft polymers of gelatin with other high molecular compounds, proteins such as albumin, casein, etc.; cellulose derivatives such as hydroxyethyl cellulose, carboxymethyl cellulose, cellulose ester sulfate, etc.; sodium alginate; sugar derivatives such as starch derivatives; monomers or polymers such as polyvinyl alcohol, polyvinyl alcohol partial acetal, poly-N-vinyl pyrrolidone, polyacrylic acid, polymethacrylic acid, polyacrylamide, polyvinyl imidazole, polyvinyl pyrazole, etc., and the like can be used.

As gelatin, lime-processed gelatin as well as acid-treated gelatin can be used. Hydrolyzates or products of enzymatic decomposition of gelatin may also be used.

An acid polymer may be added to the present light-sensitive material. Such an acid polymer may be added in the form of a basic substance such as a tertiary amine and an alkali hydroxide.

The acid polymer which may be used in the present invention is a compound containing an acid group having a pKa of 9 or less. As such a compound, a polymer containing a carboxyl group, a sulfoxyl group, or an endiole group can preferably be used. Specific examples of such a polymer include polymers of acrylic acid and methacrylic acid or maleic acid, and partial esters or acid anhydrides thereof as described in U.S. Pat. No. 3,362,819; copolymers of acrylic acid and acrylic ester as described in French Pat. No. 2,290,699; and latex type acid polymers as described in U.S. Pat. No. 4,139,383 and *Research Disclosure*, No. 16102 (1977), and the like.

Besides the above acid polymers, those described in U.S. Pat. No. 4,088,493, and Japanese Patent Application (OPI) Nos. 153739/77, 1023/78, 4540/78, 4541/78 and 4542/78 may be used.

A preferred example of such an acid polymer is an acid polymer containing acrylic acid as an acid group. The monomer component to be polymerized with the acrylic acid is preferably an alkyl acrylate or alkyl methacrylate.

A particularly preferred acid polymer is in the form of a water-dispersed latex. Such a water-dispersed latex can easily be mixed with a water-soluble binder such as gelatin, polyacrylamide, and polyvinyl alcohol without causing aggregation or precipitation. The tertiary amine for forming a salt of an acid polymer is preferably used in an amount to neutralize 10 to 100 mol %, and more preferably 20 to 80% of the acid group of the acid polymer.

In the present invention, when a tertiary amine salt of an acid polymer is incorporated in the photographic light-sensitive material, it may be incorporated in a silver halide emulsion or other light-insensitive hydrophilic colloid layers. Preferred layers in which the tertiary amine salt is incorporated are a light-insensitive hydrophilic colloid layer and a substantially hydrophobic polymer layer which is adjacent to the emulsion layer.

The optimum amount of the tertiary amine salt of an acid polymer of the present invention to be coated is preferably selected depending on the proportion of the acid content in the polymer, processing conditions, and amount of various chemicals to be added. A suitable amount is in the range of from 10 mg/m$^2$ to 10 g/m$^2$, and preferably from 20 mg/m$^2$ to 3 g/m$^2$. A suitable content of the acid group is in the range of from 0.1 mmol/m$^2$ to 100 mmol/m$^2$, and preferably from 0.5 mmol/m$^2$ to 50 mmol/m$^2$ The pH of the surface of the film of the silver halide light-sensitive material containing a tertiary amine salt of an acid polymer of the present invention is generally in the range of from 5.0 to 6.8.

The present light-sensitive material may comprise the following developing agents:

For example, ascorbic acids such as L-ascorbic acid; dihydroxybenzenes such as hydroquinone; 3-pyrazolidones such as 1-phenyl-3-pyrazolidone, 4,4-dimethyl-1-phenyl-3-pyrazolidone, etc.; aminophenols such as N-methyl-p-aminophenol, and the like may be used singly or in combination.

The above described dihydroxybenzenes and ascorbic acids are preferably used in combination with the 3-pyrazolidones or aminophenols.

Preferred examples of such a combination include a combination of ascorbic acids with 3-pyrazolidones, a combination of ascorbic acids with aminophenols, a combination of dihydroxybenzenes with 3-pyrazolidones, and a combination of dihydroxybenzenes with aminophenols.

In the present invention, when two or more developing agents are used in combination, dihydroxybenzenes or ascorbic acids are used in an amount of from 1 to 50 mol, preferably from 2 to 50 mol, and more preferably from 3 to 20 mol per mol of 3-pyrazolidones or aminophenols.

Alternatively, a combination of three compounds, e.g., ascorbic acids, 3-pyrazolidones and aminophenols may also be used.

The amount of such a combination of two or more developing agents to be added to the light-sensitive material is from 0.2 to 0.001 mol, and preferably from 0.1 to 0.005 mol per mol of silver.

The silver halide emulsion to be used in the present invention may optionally be chemically sensitized. As the chemical sensitization process for the silver halide emulsion there have heretofore been known sulfur sensitization, reduction sensitization and noble metal sensitization. These sensitization processes can be used singly or in combination.

A typical example among the noble metal sensitization processes is gold sensitization which uses a gold compound, mainly a gold complex salt. Such a gold sensitization may use a compound containing a complex salt of noble metal other than gold, such as platinum, palladium and iridium. Specific examples of such a noble metal sensitization are described in U.S. Pat. No. 2,448,060 and British Pat. No. 618,061.

As sulfur sensitizing agents, there may be used various sulfur compounds such as thiosulfate, thiourea, thiazole, and rhodanine as well as sulfur compounds contained in gelatin.

As reduction sensitizing agents, there may be used various compounds such as stannous salt, amine, formamidinesulfinic acid and silane compound.

The light-sensitive material to be used in the present invention may contain a sensitizing dye as described in U.S. Pat. No. 4,243,739 (e.g., a cyanine dye and a merocyanine dye, etc.) for the purpose of increasing sensitivity.

For example, if a cationic due is used, a cyanine, hemicyanine or rhodacyanine dye is preferably used. Particularly preferred examples of such a dye are shown hereinafter.

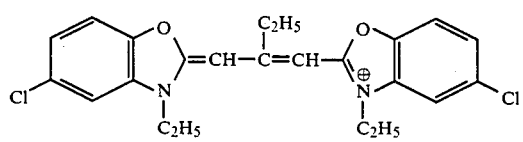

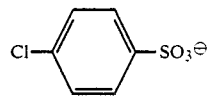

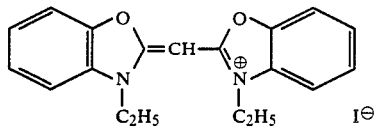

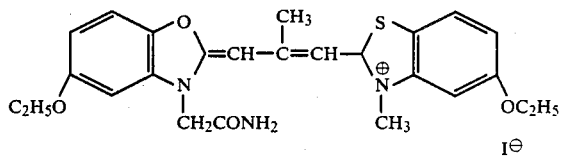

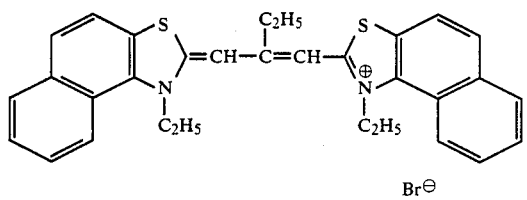

These sensitizing dyes may be used singly or in combination. Combinations of sensitizing dyes are often used for the purpose of supersensitization. The present photographic emulsion may contain a dye which itself has no photosensitization effect or a substance which does not substantially absorb visible light and exhibit supersensitization as well as a supersensitizing dye.

Examples of useful sensitizing dyes, combinations of dyes exhibiting supersensitization and substances exhibiting supersensitization are described in *Research Disclosure*, No. 17643, Vol. 176, page 23, IV-J (December, 1978).

The present light-sensitive material may contain various compounds in order to prevent fogging during production, storage or photographic processing thereof or to stabilize photographic properties thereof. That is, many compounds known as fog inhibitors or stabilizers such as azoles (e.g., benzothiazolium salts, nitroindazole, chlorobenzimidazole, bromobenzimidazole, mercaptothiazole, mercaptobenzothiazole, mercaptothiadiazole, aminotriazole, benzothiazole, nitrobenzotriazole, etc.), mercaptopyrimidines, mercaptotriazines, thioketo compounds (e.g., oxazolinethione, etc.), azaindenes (e.g., triazaindene, tetraazaindene (particularly 4-hydroxy-substituted (1,3,3a,7)tetraazaindene, pentaazaindene, etc.), benzenethiosulfonic acid, benzenesulfinic acid, and benzenesulfonic acid can be used. Preferred among these compounds are benzotriazoles such as 5-methylbenzotriazole and nitroindazole such as 5-nitroindazole. Alternatively, these compounds may be contained in the processing solutions.

The present photographic light-sensitive material may contain an inorganic or organic hardener in the photographic emulsion layer or other hydrophilic colloid layers. For example, chromium salts such as chrome alum and chromium acetate; aldehydes such as formaldehyde, glyoxal and glutaraldehyde; N-methylol compounds such as dimethylolurea and methyloldimethylhydantoin; dioxane derivatives such as 2,3-dihydroxydioxane; active vinyl compounds such as 1,3,5- triacryloylhexahydro-s-triazine and 1,3-vinylsulfonyl-2-propanol; active halogen compounds such as 2,4-dichloro-6-hydroxy-s-triazine; mucohalogenic acids such as mucochloric acid and mucophenoxychloric acid; epoxy compounds such as tetramethylene glycol diglycidyl ether; and isocyanate compounds such as hexamethylenediisocyanate can be used singly or in combination.

The photographic emulsion layer or other hydrophilic colloid layers in the light-sensitive material prepared in accordance with the present invention may contain various surface active agents for various purposes such as helping coating, preventing electrification, improving sliding properties, improving emulsion dispersion, preventing adhesion, and improving photographic properties (e.g., acceleration of development, increasing contrast and sensitization).

For example, there may be used nonionic surface active agents such as a saponin (steroid system), alkylene oxide derivatives (e.g., polyethylene glycol, polyethylene glycol/polypropylene glycol condensation products, polyethylene glycol alkyl ethers or polyethylene glycol aryl ethers, polyethylene glycol esters, polyethylene glycol sorbitan esters, polyalkylene glycol alkylamine or amide, and polyethylene oxide addition products of silicone), glycidol derivatives (e.g., polyglyceride alkenylsuccinate and alkylphenol polyglyceride), aliphatic esters of polyvalent alcohol, and alkyl esters of sugar, anionic surface active agents containing an acid group such as a carboxyl group, a sulfo group, a phospho group, a sulfuric ester group, and a phosphoric ester group (e.g., alkyl carboxylate, alkyl sulfonate, alkylbenzenesulfonate, alkylnaphthalenesulfonate, alkylsulfuric ester, alkylphosphoric ester, N-acyl-N-alkyltaurine, sulfosuccinic ester, sulfoalkylpolyoxyethylene alkyl phenyl ether, and polyoxyethylene alkylphosphoric ester), amphoteric surface active agents such as amino acid, aminoalkylsulfonic acid, aminoalkylsulfuric or aminoalkylphosphoric ester, alkylbetaine, and amine oxide, and cationic surface active agents such as alkylamine salts, aliphatic or aromatic quaternary ammonium salts, heterocyclic quaternary ammonium salts (e.g., pyridinium and imidazolium), and phosphonium or sulfonium salts containing an aliphatic group or a heterocyclic group.

A surface active agent which is particularly preferably used in the present invention is a polyalkylene oxide having a molecular weight of 600 or more as described in Japanese Patent Publication No. 9412/83. In order to stabilize dimension, the present silver halide photographic material may also contain a polymer latex such as polyalkyl acrylate.

In order to obtain excellent photographic properties such as superhigh contrast and high sensitivity using the present silver halide light-sensitive material, a stable developing solution can be used. There is no need to use the conventional infectious developing solution or high alkali developing solution having a pH of nearly 13 as described in U.S. Pat. No. 2,419,975.

That is, in order to obtain a sufficiently superhigh contrast negative image, the present silver halide light-sensitive material can be processed by a developing solution containing as a preservative 0.15 mol/l or more of sulfite ions and having a pH of from 10.5 to 12.3, and preferably from 11.0 to 12.0.

The developing agent which can be used in the present invention is not specifically limited. For example, there may be used, singly or in combination, dihydroxybenzenes such as hydroquinone, 3-pyrazolidones such as 1-phenyl-3-pyrazolidone and 4,4-dimethyl-1-phenyl-3-pyrazolidone and aminophenols such as N-methyl-p-aminophenol.

The present silver halide light-sensitive material is particularly adapted to be processed by a developing solution containing as a developing agent a dihydroxybenzene and as an auxiliary developing agent a 3-pyrazolidone or aminophenol. Preferably, such a developing solution contains from 0.05 to 0.5 mol/l of a dihydroxybenzene and 0.06 mol/l or less of a 3-pyrazolidone or aminophenol in combination.

As described in U.S. Pat. No. 4,269,929, an amine can be added to the developing solution to raise the developing speed, thereby shortening the developing time.

Furthermore, a pH buffer such as sucrose, 5-sulfosalicylic acid, sulfite, carbonate, borate, and phosphate, of alkali metals and a development inhibitor or antifoggant such as bromide, iodide, and an organic antifoggant (particularly preferably nitroindazole or benzotriazole) may be added to the developing solution. The developing solution may optionally contain a hard water softening agent, a dissolving aid, a color controlling agent, a development accelerator, a surface active agent (particularly preferably the above mentioned polyalkylene oxide), a defoaming agent, a hardener, and an agent for preventing film from staining with silver (e.g., 2-mercaptobenzimidazolesulfonic acid).

As a fixing solution there may be used a common composition. As a fixing agent there may be used a thiosulfate, thiocyanate or organic sulfur compound known to have an effect as a fixing agent. The fixing solution may contain as a hardener a water-soluble aluminum salt or the like.

The processing temperature in the present invention is generally selected from between about 18° C. and 50° C.

The photographic processing is preferably effected by means of an automatic developing machine. Even if the total processing time between the input of the light-sensitive material in an automatic developing machine and the output of the light-sensitive material from the automatic developing machine is set from 90 to 120 seconds, the present invention can provide a sufficiently superhigh contrast with a negative gradation.

As described above, the compound of formula (I) can be combined with a negative type emulsion to be used in a high contrast light-sensitive material. Alternatively, the compound of formula (I) can be combined with an internal latent image type silver halide emulsion. Embodiments of such a combination will be further illustrated hereinafter. In this case, the compound of formula (I) is preferably incorporated in an internal latent image type silver halide emulsion layer. However, the compound may be incorporated in a hydrophilic colloid layer adjacent to the internal latent image type silver halide emulsion layer. Examples of such an adjacent layer include a color former layer, an interlayer, a filter layer, a protective layer, an antihalation layer, and any other layers which do not hinder a nucleating agent from diffusion into the silver halide grains in the silver halide emulsion layer.

The content of the compound of formula (I) in the layer is such that when the internal latent image type emulsion is developed by a surface developing agent, it provides a sufficient maximum density (e.g., silver density of 1.0 or more). In practice, the value varies with the properties of the silver halide emulsion used, chemical structure of the nucleating agent, and developing conditions. Therefore, a suitable content of the compound represented by formula (I) can be varied over a wide range. The practically useful range of the content of the compound represented by formula (I) is from about 0.005 to about 500 mg, preferably from about 0.01 to about 100 mg, per mol of silver in the internal latent image type silver halide emulsion. If the compound of formula (I) is incorporated in the hydrophilic colloid layer adjacent to the emulsion layer, the amount of the compound to be used may be the above mentioned value based on the amount of silver contained in the same area of the internal latent image type emulsion layer. The term "internal latent image type silver halide emulsion" as used herein can be definitely defined by the fact that it provides a greater maximum density when developed by an "internal type" developing solution than when developed by a "surface type" developing solution after being exposed to light. The internal latent image type emulsion suitable for the present invention is such that the maximum density obtained when a transparent support on which it has been coated is developed by the following developing solution A (internal type) at a temperature of 20° C. for 3 minutes after being exposed to light for a fixed period of time of 0.01 to 1 second is at least 5 times that obtained when the same material is developed by the following developing solution B (surface type) at a temperature of 20° C. for 4 minutes after being subjected to light exposure under the same conditions. The measurement of the maximum density is conducted by the ordinary method.

| Developing Solution A: | |
|---|---|
| Hydroquinone | 15 g |
| Monomethyl-p-aminophenol Sesquisulfate | 15 g |
| Sodium Sulfite | 50 g |
| Potassium Bromide | 10 g |
| Sodium Hydroxide | 25 g |
| Sodium Thiosulfate | 20 g |
| Water to make | 1 liter |
| Developing Solution B: | |
| p-Oxyphenyl Glycine | 10 g |
| Sodium Carbonate | 100 g |
| Water to make | 1 liter |

The internal latent image type silver halide emulsion to be used in the present invention is a hydrophilic colloid dispersion comprising silver chloride, silver bromide, silver chlorobromide, silver iodobromide, silver chloroiodobromide, or a mixture thereof. The halogen composition of the emulsion is selected depending on the purpose of use and processing conditions of the light-sensitive material. In particular, silver bromide, silver iodobromide or silver chloroiodobromide containing 10 mol % or less of iodide and 30 mol % or less of chloride is preferably used. Besides the emulsions described in U.S. Pat. No. 2,592,250, as such an emulsion there may be used a conversion type emulsion, core/shell type emulsion, and emulsion doped with a different metal as described in British Pat. No. 1,027,146, and U.S. Pat. Nos. 3,206,313, 3,511,662, 3,447,927, 3,737,313, 3,761,276 and 3,935,014. However, the present invention should not be construed as being limited to these emulsions.

The present light-sensitive material may comprise various photographic supports readily determined by those skilled in the art. The silver halide emulsion can be coated on one or both sides of the support.

In the present light-sensitive material, the silver halide emulsion layer or other hydrophilic colloid layers may comprise other additives, particularly compounds useful for the photographic emulsion such as a lubricant, a stabilizer, a hardener, a sensitizer, a light absorbing dye, a plasticizer, and the like.

In the present invention, the silver halide emulsion may comprise a compound which releases iodine ions (e.g., potassium iodide). Alternatively, a developing solution containing iodine ions can be used to obtain a desired image.

In the present light-sensitive material, the internal latent image type emulsion may be spectrally sensitized by a sensitizing dye to a relatively long wavelength region such as blue light, green light, red light, and infrared light. As such a sensitizing dye, there may be used a cyanine dye, a merocyanine dye, a complex cyanine dye, a complex merocyanine dye, a holopolar cyanine dye, a styryl dye, a hemicyanine dye, an oxonol dye, a hemioxonol dye, or the like. These sensitizing dyes include cyanine dyes and merocyanine dyes as described in Japanese Patent Application (OPI) Nos. 40638/84, 40636/84 and 38739/84.

The present light-sensitive material may comprise a color image forming coupler as a coloring agent. Alternatively, the present light-sensitive material may be developed by a developing solution containing such a color image forming coupler.

In the present invention, a developing agent such as hydroxybenzene (e.g., hydroquinone), aminophenol and 3-pyrazolidone may be contained in the emulsion or light-sensitive material.

The photographic emulsion to be used in the present invention may be used in combination with a dye image donor compound for a diffusion transfer color photographic process (coloring agent) which releases a diffusible dye in response to development of silver halide to provide a desired transfer image on the image receiving layer after a proper development. As such a coloring agent for a color diffusion transfer process, there have been known many compounds. For example, there may be used compounds as described in U.S. Pat. Nos. 3,227,551, 3,227,554, 3,443,939, 3,443,940, 3,443,930, 3,443,943, 3,628,952, 3,844,785, 3,658,524, 3,698,897, 3,725,062, 3,728,113, 3,751,406, 3,929,760, 3,931,144, 3,932,381, 3,928,312, 4,013,633, 3,932,380, 3,954,476, 3,942,987, 4,013,635, 4,053,312, 4,055,428, 4,268,625 and 4,336,322, U.S. Pat. No. B 351,673, British Pat. Nos. 840,731, 904,364 and 1,038,331, West German Patent Application (OLS) Nos. 1,930,215, 2,214,381, 2,228,361, 2,317,134 and 2,402,900, French Pat. No. 2,284,140, Japanese Patent Application (OPI) Nos. 46730/78, 130122/79, 16130/81, 650/82, 4043/82, 104343/76, 12642/81 and 143323/78. In particular, a coloring agent of the type which is initially nondiffusible but undergoes cleavage upon a redox reaction with an oxide of a developing agent (or electron transferring agent) to release a diffusible dye (hereinafter referred to as "DRR compound") is preferably used. A DRR compound containing an N-substituted sulfamoyl group is most preferably used. Furthermore, examples of DRR compounds which can be preferably used in combination with the present nucleating agent include DRR compounds containing an o-hydroxyarylsulfamoyl group as described in U.S. Pat. Nos. 4,055,428, 4,053,312 and 4,336,322 and DRR compounds containing a redox nucleus as described in Japanese Patent Application (OPI) No. 149328/78. The combined use of such a DRR compound brings a remarkably small temperature dependency upon processing in particular.

Specific examples of other DRR compounds include 1-hydroxy-2-tetramethylenesulfamoyl-4-[3'-methyl-4'-(2''-hydroxy-4''-methyl-5''-hexadecyloxyphenylsulfamoyl) phenylazo]naphthalene as a magenta dye image forming substance and 1-phenyl-3-cyano-4-{3'-[2''-hydroxy-4''-methyl-5''-(2''', 4'''-di-tert-pentylphenoxyacetamino) phenylsulfamoyl]phenylazo}-5-pyrazolone as a yellow dye image forming substance.

The light-sensitive material comprising the present internal latent image type emulsion can be developed by a surface developing solution to provide a direct positive image. The surface developing solution is adapted to have its development process caused substantially by latent images or a fog nucleus on the surface of silver halide grain. Such a surface developing solution is preferably free of a silver halide dissolving agent. However, the developing solution may contain some silver halide dissolving agent (e.g., sulfite) so far as latent images do not substantially contribute to development until development by the surface development center of silver halide grain.

In order to develop the light-sensitive material comprising the present internal latent image type emulsion, there may be used, singly or in combination, various known developing agents such as polyhydroxybenzene (e.g., hydroquinone, 2-chlorohydroquinone, 2-methylhydroquinone, catechol, and pyrogallol, aminophenol (e.g., p-aminophenol, N-methyl-p-aminophenol and 2,4-diaminophenol), 3-pyrazolidone (e.g., 1-phenyl-3-pyrazolidone, 4,4-dimethyl-1-phenyl-3-pyrazolidone, 4,4-dihydroxymethyl-1-phenyl-3-pyrazolidone, 4-methyl-4-hydroxymethyl-1-phenyl-3-pyrazolidone, and 4-methyl-4-hydroxymethyl-1-p-tolyl-3-pyrazolidone), and ascorbic acid. In order to obtain a dye image by a dye forming coupler, there may be used an aromatic primary amine developing agent, and preferably a p-phenylenediamine developing agent. Specific examples of such developing agents include 4-amino-3-methyl-N,N-diethylaniline hydrochloride, N,N-diethyl-p-phenylenediamine, 3-methyl-4-amino-N-ethyl-N-β-(methanesulfonamido)ethylaniline, 3-methyl-4-amino-N-ethyl-N-(β-sulfoethyl)aniline, 3-ethoxy-4-amino-N-ethyl-N-(β-sulfoethyl)aniline, and 4-amino-N-ethyl-N-(β-hydroxyethyl)aniline. Such a developing agent may be incorporated in an alkaline processing composition (processing element) or a proper layer in the light-sensitive material.

In the present invention, if a DRR compound is used, any silver halide developing agent (or electron transferring agent) which can cross-oxidize the DRR compound can be used. In particular, 3-pyrazolidones are preferably used.

The present developing solution may comprise sodium sulfite, potassium sulfite, ascorbic acid, reductone such as piperidinohexose reductone or the like as a preservative.

The present developing solution may also comprise an alkali agent and buffer such as sodium hydroxide, potassium hydroxide, sodium carbonate, potassium carbonate, trisodium phosphate, and sodium metaborate. The content of such agents is preferably selected so that the pH of the developing solution reaches from 10 to 13.

The present developing solution may comprise a color development accelerator such as benzyl alcohol.

Furthermore, in order to further lower the minimum density of the direct positive image, the present developing solution may advantageously comprise a compound which is commonly used as a fog inhibitor, such as a benzimidazole (e.g., 5-nitrobenzimidazole), and a benzotriazole (e.g., benzotriazole and 5-methylbenzotriazole).

The present light-sensitive material can also be processed with a viscous developing solution.

Such a viscous developing solution is a liquid composition containing components necessary for development of the silver halide emulsion and formation of diffusion transfer color images. The solvent of the liquid composition mainly comprises water, and optionally a hydrophilic solvent such as methanol and methyl cellosolve. The processing composition contains an alkali in an amount enough to maintain a pH required to cause development of the emulsion layer and neutralize acids produced in the step of development and various processes for formation of dye images (e.g., hydrohalogenic acid such as hydrobromic acid and carboxylic acid such as acetic acid). As such an alkali, there may be used lithium hydroxide, sodium hydroxide, potassium hydroxide, dispersion of potassium hydroxide, tetramethylammonium hydroxide, sodium carbonate, trisodium phosphate, diethylamine, and other alkali metal or alkaline earth metal salts or amines. In particular, a caustic alkali having a concentration which provides a pH of about 12 or more (preferably about 14 or more) at room temperature is preferably contained in the processing composition. More preferably, the present processing composition contains a hydrophilic polymer such as high molecular polyvinyl alcohol, hydroxyethyl cellulose, and sodium carboxymethyl cellulose. These polymers are preferably used in such a manner that the viscosity of the processing composition reaches 1 poise or more, and preferably 500 to 1,000 poise at room temperature.

The processing composition may also comprise a light-absorbing substance such as carbon black and a pH indicating dye or a desensitizer as described in U.S. Pat. No. 3,579,333 in order to prevent the silver halide emulsion from being fogged during or after processing. This is particularly advantageous in the case where the processing composition is used for a monosheet film unit. Furthermore, the processing composition may comprise a development inhibitor such as benzotriazole.

The above mentioned processing composition is preferably used as it is contained in a rupturable container as described in U.S. Pat. Nos. 2,543,181, 2,643,886, 2,653,732, 2,723,051, 3,056,491, 3,056,492 and 3,152,515.

If the light-sensitive material of the present invention is used in a diffusion transfer photographic process, it is preferably in the form of a film unit. A photographic film unit which is arranged to be processed by being passed between a pair of juxtaposed pressure members essentially consists of the following three elements:

(1) light-sensitive element containing the present nucleating agent;
(2) image receiving element; and
(3) processing element containing in a film unit, such as a rupturable container, a means for releasing an alkaline processing composition, and optionally a silver halide developing agent.

A preferred embodiment of such a photographic film unit is an integrated lamination type as disclosed in Belgian Pat. No. 757,959. In accordance with the embodiment, an image receiving layer, a substantially transparent light-reflecting layer (e.g., $TiO_2$ layer and carbon black layer), and a light-sensitive element consisting of a single or a plurality of silver halide light-sensitive layers combined with a DRR compound are coated on a transparent support in this order. A transparent cover sheet is then superposed on the lamination in a face-to-face manner. A rupturable container containing an alkaline processing composition containing an opacifier such as carbon black is disposed adjacent to the top layer in the light-sensitive layer and the transparent cover sheet. Such a film unit is exposed to light through the transparent cover sheet. When the film unit is withdrawn from the camera, the container is ruptured by the pressure members so that the processing composition (containing an opacifier) is spread between the protective layer on the light-sensitive layer and the cover sheet. This screens the film unit from light, and development progresses. In the cover sheet, a neutralization layer, and optionally a neutralization speed adjusting layer (timing layer) are preferably coated on a transparent support in this order.

Another useful integrated lamination type photographic film unit which can use a DRR compound or a diffusible dye releasing coupler is described in U.S. Pat. Nos. 3,415,644, 3,415,645, 3,415,646, 3,647,487 and 3,635,707, and German Patent Application (OLS) No. 2,426,980.

The present invention will be further illustrated in the following examples, but the present invention should not be construed as being limited thereto.

Unless otherwise indicated, all percents, ratios, etc., are by weight.

EXAMPLE 1

Grains were prepared by means of a control double jet. Three kinds of monodispersed negative type silver halide emulsions A to C shown in Table 1 were prepared. In the preparation of the emulsions A to C, the temperature was adjusted to that the average grain size reached 0.25 μm. These emulsions were then washed with water in accordance with the ordinary method to remove soluble salts therefrom. 4-Hydroxy-6-methyl-1,3,3a,7-tetraazaindene was added to the material as a stabilizer.

These three kinds of silver halide emulsions were divided into various groups. As shown in Table 1, the Present Compounds 5 and 6 and Comparative Compounds a and b were added to these emulsions. A sodium salt of 5,5'-dichloro-9-ethyl-3,3'-bis(3-sulfopropyl)oxacarbocyanine, a dispersion of polyethyl acrylate, polyethylene glycol, 1,3-vinylsulfonyl-2-propanol, and Compound 9 were added to each emulsion as sensitizing dyes. These emulsions were coated on a polyethylene terephthalate base in an amount such that the amount of silver reached 3.4 $g/m^2$.

These films thus prepared were exposed to light through an exposure wedge for sensitometry by means of a 150-line magenta contact screen. These films were than developed by a developing solution having the following composition at a temperature of 38° C. for 20 seconds, and subjected to stopping, fixing, rinsing, and drying. The results are shown in Table 1.

| Developing Solution: | |
|---|---|
| Tetrasodium Ethylenediaminetetraacetate | 1.0 g |
| Sodium Hydroxide | 13.0 g |
| Tribasic Potassium Phosphate | 74.0 g |
| Potassium Sulfite | 90.0 g |
| 3-Diethylamino-1-propanol | 15.0 g |
| N—Methyl-p-aminophenol · ½ Sulfate | 0.8 g |
| Hydroquinone | 35.0 g |
| 5-Methylbenzotriazole | 0.5 g |
| Sodium Bromide | 3.0 g |
| Water to make | 1 liter |
| pH | 11.6 |

TABLE 1

| No. | Emulsion Type | Halogen Composition | Comparative Compound Type | Added* Amount | Present Compound Type | Added* Amount | γ** | Dot*** Quality |
|---|---|---|---|---|---|---|---|---|
| 1 | A | AgBrI | a | $2.5 \times 10^{-3}$ | — | — | 13 | 3 |
| 2 | | (I = 1 mol %) | b | $2.5 \times 10^{-4}$ | — | — | 19 | 4 |
| 3 | | | — | — | 5 | $1.2 \times 10^{-4}$ | 22 | 5 |
| 4 | | | — | — | 6 | " | 21 | 5 |
| 5 | B | AgBr | a | $2.5 \times 10^{-3}$ | — | — | 11 | 3 |
| 6 | | | b | $2.5 \times 10^{-4}$ | — | — | 15 | 4 |
| 7 | | | — | — | 5 | $1.2 \times 10^{-4}$ | 20 | 5 |
| 8 | | | — | — | 6 | " | 19 | 5 |
| 9 | C | AgBrCl | a | $2.5 \times 10^{-3}$ | — | — | 11 | 3 |
| 10 | | (Br = 50 mol %) | b | $2.5 \times 10^{-4}$ | — | — | 16 | 3 |
| 11 | | — | — | 5 | | $1.2 \times 10^{-4}$ | 20 | 4 |
| 12 | | — | — | | | 6 " | 19 | 4 |

It is clearly seen from the results of Table 1 that the present compound can provide a high contrast gradation and an excellent dot quality even when added in less amount than the Comparative Compounds a and b.

EXAMPLE 2

Grains were prepared in the presence of rhodium ammonium chloride. A monodispersed negative type silver chlorobromide emulsion D (bromine content: 30 mol%) comprising $5.0 \times 10^{-5}$ mol/mol Ag was prepared. (Average grain size: 0.20 μm).

These emulsions thus prepared were washed with water in accordance with the ordinary method to remove soluble salts therefrom. 4-Hydroxy-6-methyl-1,3,3a,7-tetraazaindene was added to these emulsions as a stabilizer.

These emulsions were divided into groups. As shown in Table 2, the Present Compound 5 and the Comparative Compound a were added to these emulsions. A dispersion of polyethylene acrylate, and a sodium salt of 2-hydroxy-4,6-dichloro-1,3,5-triazine were then added to these emulsions. These emulsions were coated on a polyethylene terephthalate film in an amount such that the amount of silver reached 3.5 $g/m^2$.

These films were then exposed to light through an exposure wedge for sensitometry by means of a Dainihon Screen's P-607 Type Printer. These films were developed by the developing solution described in Example 1 at a temperature of 38° C. for 20 seconds, and then subjected to stopping, fixing, rinsing, and drying. The results are shown in Table 2.

TABLE 2

| No. | Emulsion Type | Rh Content* | Comparative Compound Type | Added* Amount | Present Compound Type | Added* Amount | γ** | Extract Letter Image Quality*** |
|---|---|---|---|---|---|---|---|---|
| 13 | D | 5 × 10⁻⁵ | a | 1.0 × 10⁻² | — | — | 6 | 1 |
| 14 | " | " | — | — | 5 | 3 × 10⁻³ | 16 | 4 |

*The unit of Rh content and added amount are represented by mol/mol·Ag.
**γ is as defined in Example 1.
***Extract letter image quality is a functional evaluation of reproduction of letters of specified sizes on development on a lamination of a laminate base/a film on which a line positive image is formed (line original)/a laminate base/a film on which a dot image is formed (dot original) when it is kept intimate in such a manner that the protective layer in each film specimen is superimposed on the dot original face-to-face, exposed to light in such a manner that 50% dot area gives 50% dot area on the film specimen, and then processed in the manner as described above. The capability of reproducing a 30-μm width letter on the line original is valued as "5". The capability of reproducing letters of 150 μm or larger width is valued as "1". Thus, steps 4, 3 and 2 are set between 5 and 1. "2" is the lowest limit which can be practically used.

It is clearly seen from the results of Table 2 that the present compound provides a remarkably high contrast and an excellent extract letter image quality with respect to an emulsion containing a large amount of Rh as compared to the Comparative Compound a.

EXAMPLE 3

Four kinds of light-sensitive elements 1 to 4 were prepared by coating a polyethylene terephthalate transparent support with the following layers in the order of description:
(1) A mordant layer containing 3.0 g/m² of a copolymer described in U.S. Pat. No. 3,898,088 containing the repeating unit at the following proportion:

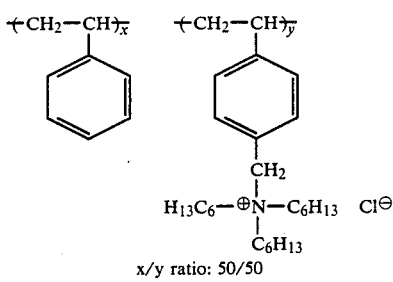

x/y ratio: 50/50 and 3.0 g/m² of gelatin.
(2) A white reflecting layer containing 20 g/m² of titanium oxide and 2.0 g/m² of gelatin.
(3) A light screen layer containing 2.70 g/m² of carbon black and 2.70 g/m² of gelatin.
(4) A layer containing 0.45 g/m² of a magenta DRR compound of the following general formula, 0.10 g/m² of diethyl laurylamide, 0.0074 g/m² of 2,5-di-t-butyl hydroquinone, and 0.76 g/m² of gelatin.

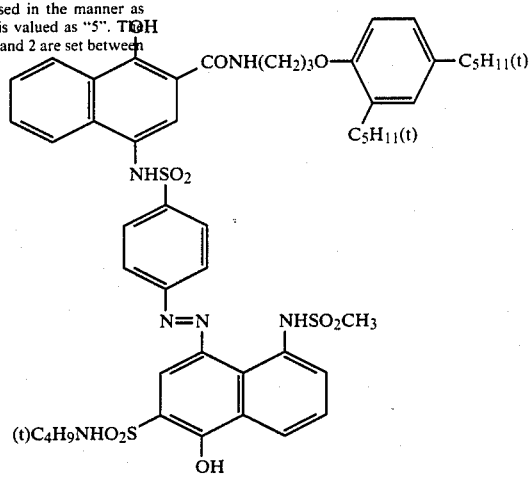

(5) A green-sensitive internal latent image type direct positive silver bromoiodide layer containing an internal latent image type emulsion (1.4 g/m² as calculated in terms of amount of silver), 1.9 mg/m² of a green-sensitive dye, 0.05 mg/m² of a nucleating agent shown in table 3, and 0.11 g/m² of sodium 5-pentadecylhydroquinone-2-sulfonate.
(6) A layer containing 0.94 g/m² of gelatin.

The above light-sensitive materials 1 to 7 and the following elements were combined. These combinations were processed.

| Processing Solution: | |
|---|---|
| 1-Phenyl-4-methyl-4-hydroxymethyl-3-pyrazolidone | 10 g |
| Methyl Hydroquinone | 0.18 g |
| 5-Methylbenzotriazole | 4.0 g |
| Sodium Sulfite (anhydrous) | 1.0 g |
| Sodium Salt of Carboxymethyl Cellulose | 40.0 g |
| Carbon Black | 150 g |
| Potassium Hydroxide (25 wt % aq. soln.) | 200 cc |
| H₂O | 550 cc |

The above processing solution was packed in a container which can be ruptured by a pressure of 0.8 g for each.

Cover Sheet:

A cover sheet was prepared by coating a polyethylene terephthalate support with 15 g/m² of a polyacrylic acid (10 wt % aqueous solution having a viscosity of 1,000 cp) as an acid polymer layer (neutralizing layer), 3.8 g/m² of acetyl cellulose (hydrolysis of 100 g of acetyl cellulose produces 39.4 g of acetyl groups) as a neutralization timing layer, and 0.2 g/m² of a copolymer of styrene and maleic anhydride (molar proportion: styrene/maleic anhydride =about 60/40, molecular weight: about 50,000).

Forced Deterioration Condition:

Two sets of the above light-sensitive elements 1 to 4 were prepared. One of the two sets was stored in a refrigerator (5° C.), and the other was allowed to stand at a temperature of 35° C. and a relative humidity of 80% for 4 days.

Processing Step:

The cover sheet thus prepared was superimposed on the above described light-sensitive sheet. The light-sensitive sheet was exposed to light through a color test chart from the cover sheet side. The above described processing solution was spread over between the two sheets by means of a pressure roller in such a manner that the thickness thereof reached 75 μm. The processing was conducted at a temperature of 25° C. The green density of the image formed on the image receiving layer was measured through the transparent support of the light-sensitive sheet by a Macbeth reflection densitometer at 1 hour after the development. The results are shown in Table 3.

TABLE 3

| Light-Sensitive Element | Nucleating Agent (added amount: mg/m²) | | $D_{max}^F$ | $S^F$ | $S^W$ |
|---|---|---|---|---|---|
| 1 (Comparison) | NA-1 | (0.3) | 1.85 | Unmeasurable | Unmeasurable |
| 2 (Comparison) | NA-2 | (0.7) | 0.30 | 100 | 105 |
| 3 (Invention) | Compound 5 | (0.7) | 1.95 | 96 | 102 |
| 4 (Invention) | Compound 8 | (0.3) | 1.90 | 99 | 120 |

$D_{max}^F$: Maximum density of positive image portion of specimens stored in the refrigerator.
$S^F$: Relative sensitivity of positive image portion of specimens stored in the refrigerator having a density of 0.5 ($S^F$ of light-sensitive element 2 being taken as 100).
$S^W$: Relative sensitivity of positive image portion having a density of 0.5 of specimens which have been allowed to stand at 35° C. and RH of 80% for 4 days ($S^F$ of light-sensitive element 2 being taken as 100)

Nucleating Agent
NA-1

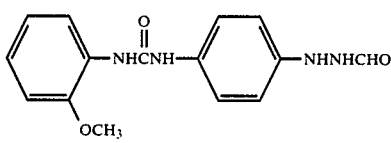

NA-2

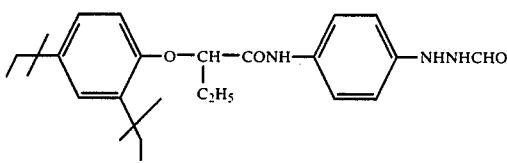

It is clearly seen from the results of Table 3 that the light-sensitive element 3, which comprises the present nucleating agent, can provide $D_{max}$ more easily than the light-sensitive element 2, which has been prepared by the conventional process, with the same added amount. It is also obvious that the light-sensitive element 4 shows less change in sensitivity than the light-sensitive element 1 after the light-sensitive material is aged.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support and at least one silver halide photographic emulsion layer formed thereon, and containing in said photographic emulsion layer or at least one hydrophilic colloid layer a compound represented by formula (I):

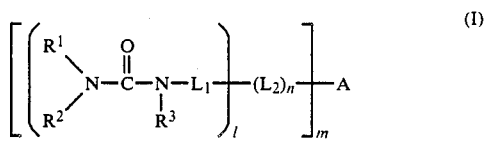

wherein $R^1$ and $R^2$ may be the same or different and each represents a hydrogen atom, an aliphatic residual group, an aromatic residual group, or a heterocyclic residual group; $R^3$ represents a hydrogen atom or an aliphatic residual group; $L_1$ represents a divalent aliphatic group, a divalent aromatic group, or a divalent heterocyclic group; $L_2$ represents —O—, —CONR—, —NRCO—, —SO$_2$NR—, —NRSO$_2$—, —OCO—, —COO—, —S—, —NR—, —CO—, —SO—, —SO$_2$—, —OCOO—, —NRCONR'—, —NRCOO—, —OCONR— or —NRSO$_2$NR'—(in which R and R' each represents a hydrogen atom, an alkyl group or an aryl group); ? and m each represents an integer of 1 or 2; n represents an integer of 0 or 1; and A represents a residual group which is obtained by removing hydrogen atoms from Ar or B in a compound represented by formula(II), provided that when m=1, one hydrogen atom is removed; when m=2, two hydrogen atoms are removed:

wherein Ar represents an aryl group; B represents a formyl group, an acyl group, an alkyl or arylsulfonyl group, an alkyl or arylsulfinyl group, a carbamoyl group, a sulfamoy group, an alkoxy or aryloxycarbonyl group, a sulfinamoyl group, an alkoxysulfonyl group, a thioacyl group, a thiocarbamoyl group, or a heterocyclic group; and $R_0$ and $R_{00}$ each represents a hydrogen atom or one of $R_0$ and $R_{00}$ represents a hydrogen atom and the other represents a substituted or unsubstituted alkyl-sulfonyl group, a substituted or unsubstituted arylsulfonyl group or a substituted or unsubstituted acyl group, with the proviso that B, $R_{00}$ and the nitrogen atom to which B and $R_{00}$ are bonded may form a partial structure of hydrazone (—N=C<), wherein A represents a group which is bonded with a nitrogen atom through a carbon atom of A, with the proviso that the compound represented by formula (I) does not contain a mercapto group.

2. A silver halide photographic material as claimed in claim 1, wherein said compound represented by formula (I) is a compound represented by formulae (III) or (IV):

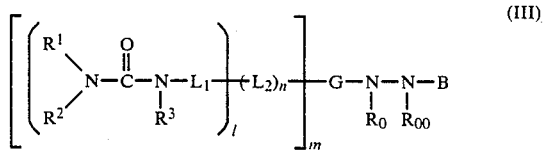

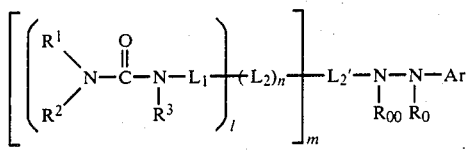

(IV)

wherein $R^1$, $R^2$, $R^3$, $L_1$, $L_2$, l, m, n, Ar, $R_0$, $R_{00}$ and B are as defined in claim 1; G represents a group formed by removing one hydrogen atom from Ar in formula (II); and $L_2'$ represents —CO—, —SO— or —SO$_2$—, with the proviso that in formula (IV $R_{00}$ may form a partial structure of hydrazone, —N=C<, together with $L_2'$ and the nitrogen atom to which $R_{00}$ and $L_2'$ are bonded.

3. A silver halide photographic material as claimed in Claim 1, wherein an amount of the compound represented by formula (I) to be used for the silver halide photographic material is from $1\times10^{-6}$ to $5\times10^{-2}$ mol per mol of silver in the silver halide emulsion.

4. A silver halide photographic material as claimed in claim 2, wherein an amount of the compound represented by formulae (III) or (IV) to be used for the silver halide photographic material is from $1\times10^{-\neq}$ to $5\times10^{-2}$ mol per mol of silver in the silver halide emulsion.

* * * * *